United States Patent [19]

Cromie

[11] 4,101,031

[45] Jul. 18, 1978

[54] PACKAGE FOR PROSTHETIC HEART VALVE OR THE LIKE

[75] Inventor: Harry W. Cromie, Pittsburgh, Pa.

[73] Assignee: Medical Engineering Corp., Racine, Wis.

[21] Appl. No.: 751,614

[22] Filed: Dec. 16, 1976

Related U.S. Application Data

[63] Continuation of Ser. No. 620,238, Oct. 6, 1975, abandoned, which is a continuation of Ser. No. 464,021, Apr. 25, 1974, abandoned.

[51] Int. Cl.² .................. B65D 81/06; B65D 85/30
[52] U.S. Cl. ..................... 206/438; 206/523; 206/588; 220/256; 220/288
[58] Field of Search ............... 206/213.1, 210, 205, 206/363, 368, 83, 439, 438, 523, 521, 418, 588, 591, 583, 593, 306; 3/1.5, 1, DIG. 3; 215/352, 350; 217/35, 53; 220/304, 288

[56] References Cited

U.S. PATENT DOCUMENTS

| 1,611,575 | 12/1926 | Aulback | 206/418 |
|---|---|---|---|
| 2,135,503 | 11/1938 | Guntrip | 206/205 |
| 2,448,401 | 8/1948 | Stone | 206/590 |
| 2,486,711 | 11/1949 | Harris | 206/583 |
| 2,620,919 | 12/1952 | Passmore | 206/83 |
| 2,645,334 | 7/1953 | Aldridge | 206/591 |
| 2,647,652 | 8/1953 | Sanford | 215/352 |
| 2,880,856 | 4/1959 | Albrecht | 206/205 |
| 3,001,639 | 9/1961 | Addis | 206/588 |
| 3,048,323 | 8/1962 | Stauffer | 206/418 |
| 3,229,813 | 1/1966 | Crowe, Jr. et al. | 206/439 |
| 3,491,376 | 1/1970 | Shiley | 3/1.5 |
| 3,847,276 | 11/1974 | Lehner | 206/45.34 |

*Primary Examiner*—Steven E. Lipman
*Assistant Examiner*—Allan N. Shoap
*Attorney, Agent, or Firm*—Thad F. Kryshak

[57] ABSTRACT

A package for a prosthetic heart valve or the like comprising a pair of separable mating package sections for receiving the heart valve and retaining it in sterile manner in biased position against a resilient pad. A separate retainer member is positioned in the package for biasing the heart valve against the pad, the retainer member being a rigid sheet having an aperture adapted to receive a portion of the valve. One of the mating package sections is provided with a shoulder which urges the retainer member into a biased position against the heart valve so that the valve is in turn biased against the resilient pad. The shoulder is adapted to slide along the surface of the retainer member so that the torque is not transmitted to the heart valve when the package sections are rotated to open or close the package.

6 Claims, 7 Drawing Figures

U.S. Patent  July 18, 1978  Sheet 1 of 2  4,101,031
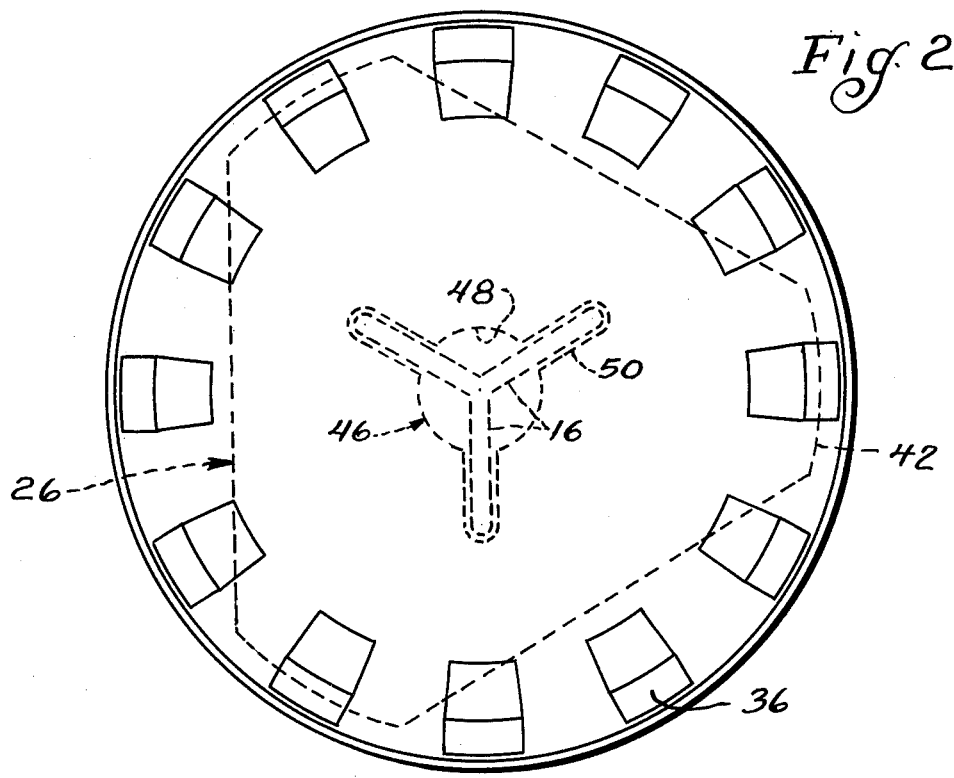
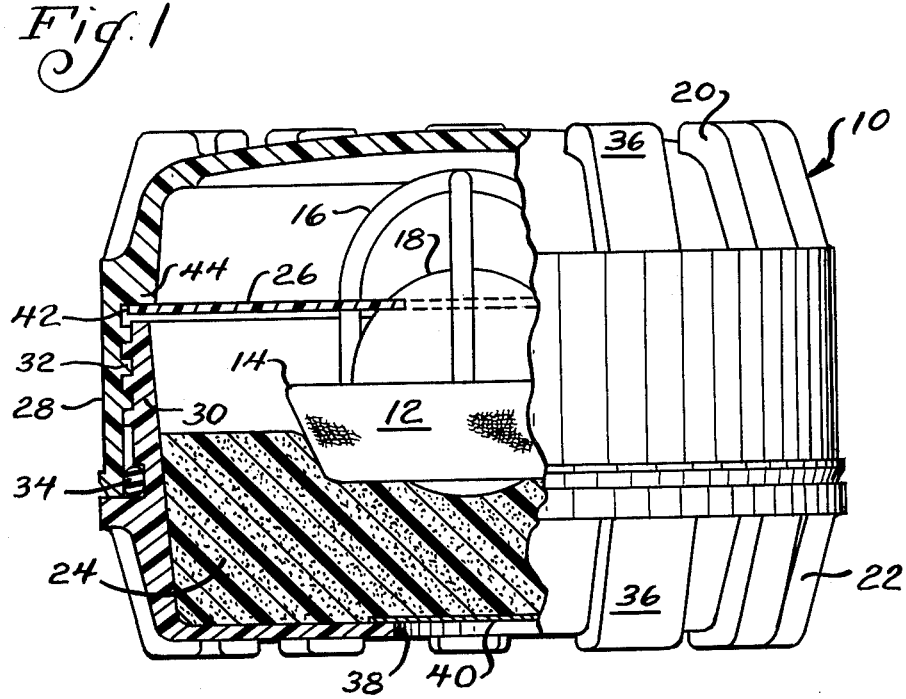

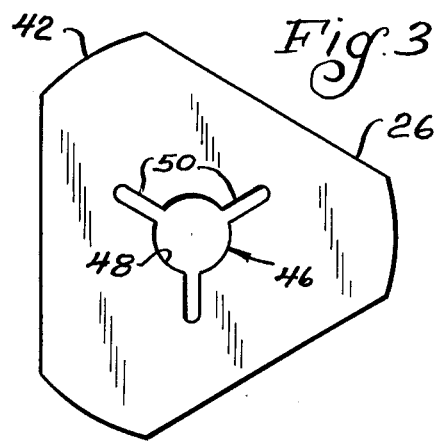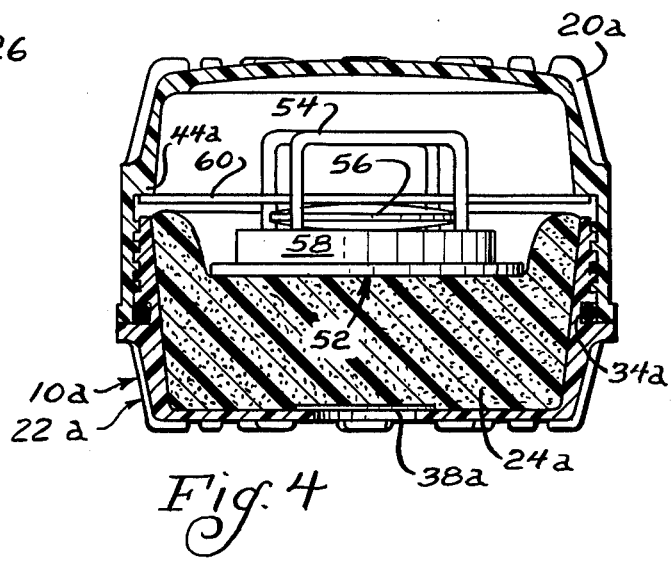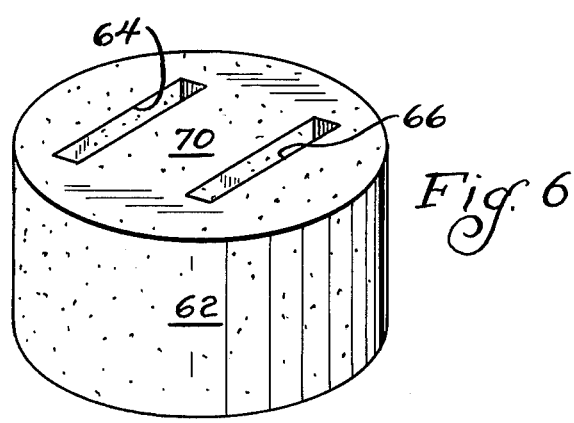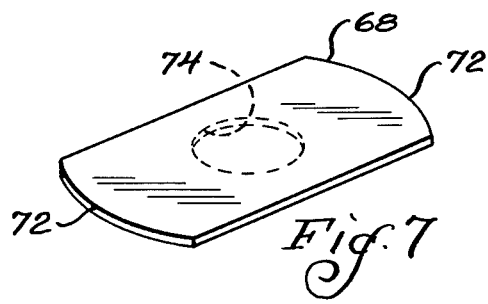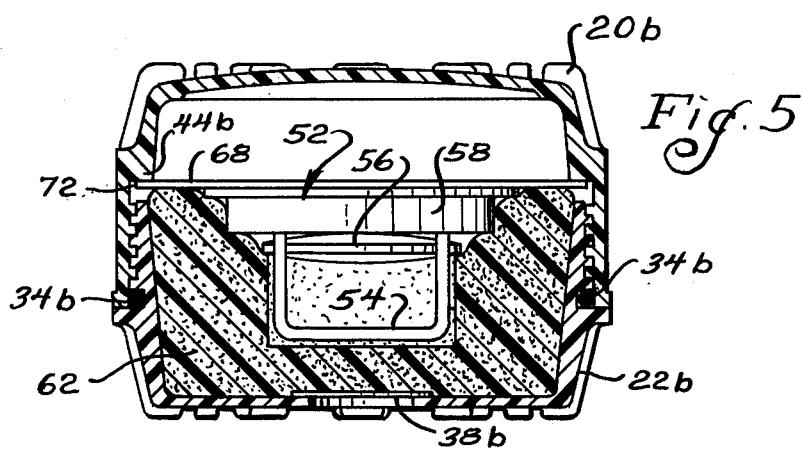

PACKAGE FOR PROSTHETIC HEART VALVE OR THE LIKE

This is a continuation of application Ser. No. 620,238, filed Oct. 6, 1975 now abandoned which is in turn a continuation of application Ser. No. 464,021, filed Apr. 25, 1974 now abandoned.

BACKGROUND OF THE INVENTION

Prosthetic heart valves are used for replacement of defective natural valves in the human heart, being emplaced by open heart surgical procedures. These devices have given thousands of patients a new lease on life, granting them an increased life span, with greater vigor and health, due to the improved blood circulation provided by the prosthetic heart valve.

Some of the most advanced models of prosthetic heart valves are coated with isotrophic, pyrolytic carbon, or a similar material, for the purpose of reducing to an absolute minimum the possibility of the formation of thromboemboli on the heart valve. Such thromboemboli, or blood clots, when they do form, can have fatal consequences to the patient.

Because of the use of the extremely brittle pyrolytic carbon coatings, and because of the general delicate construction of the heart valve, and the absolute requirement that the valve must not be bent or jolted in any way, the design of a shipping package for heart valves is a matter of critical concern.

The package must provide protection from damage by dropping or other severe jolts with an extremely high degree of reliability. The package must also protect the fragile closure member retention struts of the valve from bending during opening or closing of the package. Furthermore, it is preferable for the valve to be gas or stem sterilizable without opening the package, to avoid any possibility of damage to the valve.

One commercial package which is an attempted solution to the above requirements includes a pair of package sections with cylindrical mating portions having spaced detent members, so that the mating portions can be attached together by approximately a ⅛th turn rotation of the two package sections. One of the package sections carries a resilient pad, and the heart valve is pressed against the pad by the outer end of the other package section, for protection of the valve.

One disadvantage of the above arrangement is that, as the two package sections are relatively rotated to free the cooperating detent means on each package section for opening, a frictional torque is directly imparted from the rotating package sections to the struts of the heart valve. In certain undesirable circumstances, this may cause a slight degree of bending in the struts. Such bending could cause the movable closure member of the heart valve to bind and fail to open and close regularly and easily.

In accordance with this invention, an improved heart valve package is provided in which the above disadvantage is avoided, and in which improved protection can be provided to heart valves against rough handling in transit and the like.

DESCRIPTION OF THE INVENTION

The invention of this application relates to a package for a prosthetic heart valve, or a similar delicate item which requires an extraordinary degree of protection, comprising a pair of separable, mating package sections for receiving the heart valve, and retaining the valve in sterile manner in biased position against a resilient pad carried by one of the package sections. In accordance with this invention, a separate retainer member is positioned within the package for biasing the heart valve against the resilient pad. The retainer member is adapted for relative axial rotation with respect to the package, to prevent the transmission of torque to the heart valve through the retainer, as the mating package sections are rotated relative to each other for opening and closing the package. In other words, the separate retainer member provides added opportunity for frictional slippage of the retainer member as the package sections rotate, which reduces the torque directly imparted to the heart valve, and particularly the fragile closure member retention struts.

Preferably, each of the package sections defines a cylindrical mating portion adapted for telescopic, mating relation with the mating portion of another package section. The cylindrical mating portions each define helically mating thread and groove closing means, for closing the package sections together in a sealed package by relative axial rotation. Furthermore, annular sealing means are positioned between the cylindrical mating portions in a position to seal the helical thread and groove means from the exterior. Accordingly, the thread and groove means, when once sterilized, will tend to remain sterile during shipment. Accordingly, opening of the package presents fewer non-sterile surfaces facing the heart valve, which reduces the possibility of accidental contamination of the valve by brushing it with a non-sterile surface, or through contamination by a tiny non-sterile particle lodged between the respective thread and groove means.

The retainer is typically a rigid sheet and is biased by the package in the manner illustrated in the drawings to, in turn, bias the heart valve against the resilient pad for firm, resilient securance of the valve.

The package of this invention desirably defines an aperture which is covered by the resilient pad, in which a porous filter member is positioned on the inner wall of a package section under the resilient pad, to block entry into the aperture by non-sterile particulate matter and the like.

The aforestated Edwards valve package likewise contains apertures in its package section which are covered by the resilient pad, but the filter member is positioned on the outer wall of the package section and is intended for removal prior to autoclaving. The prior package is not intended to be shipped with its interior in sterile condition, and indeed is not capable of reliable sterile maintenance, since the paper filter member can be accidentally removed or rubbed off, due to its exposed position.

Furthermore, the resilient pad used in the package of this invention may container apertures for receiving the valve closure member retention struts, for added protection thereof.

The above advantages and features of the package of this invention are more fully described in an exemplary manner in the drawings, which are discussed below.

In the drawings,

FIG. 1 is an elevational view, taken partly in vertical section, of one embodiment of a valve package of this invention, being shown containing an aortic valve in protective, sterile sealed position.

FIG. 2 is a plan view of the valve package of this invention, with some details of the retainer member, and its relation to the retention struts of the valve, shown in phantom.

FIG. 3 is a reduced-size plan view of the retention member of FIG. 1.

FIG. 4 is an elevational view, taken in vertical section, of another embodiment of the valve package of this invention, containing a mitral valve and utilizing a different type of retainer member.

FIG. 5 is an elevational view, taken in vertical section, of a third embodiment of the valve package of this invention, also containing a mitral valve in different position.

FIG. 6 is a perspective view of the resilient pad carried within the valve package of FIG. 5.

FIG. 7 is a perspective view of the retainer member carried in the valve package of FIG. 5.

Referring to FIGS. 1 through 3, valve package 10 is shown containing a conventional mitral valve 12 of a general type currently available to thoracic surgeons for open heart surgical procedures. Valve 12 contains a valve ring 14 having a fabric portion for suturing in an excised aortic valve orifice. Valve ring 14 carries a retention cage of struts 16, within which is retained a ball closure member 18 in a position to reciprocate back and forth within the cage to open and close a flow passage through the orifice of valve ring 14.

Package 10 comprises a pair of separable, mating package sections 20, 22 for receiving the heart valve. Valve 12 can be retained in sterile manner in biased position against a resilient pad 24 made of foamed silicone rubber or the like, the biasing pressure being imparted to the heart valve by separate retainer member 26, which is a flat, roughly triangular sheet of rigid plastic or the like as shown in FIG. 3.

Package sections 20, 22 each define a cylindrical mating portion 28, 30 which each define helically mating thread and groove closure means 32 for closing the package sections together into a sealed package by relative axial rotation. Annular sealing means 34 are positioned between the cylindrical mating portions 28, 30 in a position to seal the helical thread and groove means 32 from the exterior, to retain their sterility once the package has been sterilized for the reasons described above. The annular sealing means is typically an O-ring, which runs the entire circumference of package 10.

Package sections 20, 22 both define knurls 36 to provide ease of gripping, and to elevate the main body of package section 22 off the ground a slight degree. Because of this elevation, aperture 38, which is defined in package section 22, remains in communication with the atmosphere, so that the package device can be sterilized by either autoclaving or ethylene oxide gas while resting on the ground in its normal position.

Porous filter member 40 is secured to the inner wall of package section 22 across aperture 38 to prevent the entrance of particles of contamination. Porous filter member 40 may be made out of an appropriate paper, plastic, or any other suitable filtering material capable of permitting entrance of steam and/or ethylene oxide gas for sterilization and their subsequent evacuation.

Aperture 38 is also covered by resilient pad 24, which provides further protection against the entry of contamination into the valve package.

In accordance with this invention, retainer member 26 is fabricated as a separate piece from package sections 20, 22, resting at its outer peripheral portions 42 against annular shoulder 44, which is defined in package section 20. Accordingly, shoulder 44 of package section 20 presses against periphery 42 of retainer member 26, which, in turn, biases heart valve 12 into the resilient pad 24 to provide a firm, rattle-free, resilient packaging for the heart valve 12.

Furthermore, retainer 26 is spaced from the other packaged section 22 as shown in FIG. 1, so that when the two package sections are relatively rotated, the frictional torque which is imparted to retainer 26 is at an absolute minimum, with peripheral portion 42 of the retainer sliding easily along annular shoulder 44, to prevent the transmission of torque to struts 68.

Retainer member 26 defines an aperture 46 adjacent the heart valve. In the embodiment of FIGS. 1 through 3, the aperture 46 comprises a round closure member receiving, central portion 48, which receives ball closure 18 of the valve, and permits it to be biased into closed position against valve ring 14. Aperture 46 also defines a plurality of elongated, radial, retention cage receiving portions 50 into which struts 16 fit in the manner shown in FIG. 2. Accordingly, both struts 16 and ball closure member 18 are firmly retained, and the entire valve is biased into resilient pad 24, for a maximum of shock resistance within the package.

To open package 10, package sections 20, 22 separate on relative rotation. Retainer 26 is then easily removed by grasping a peripheral portion 42 and lifting it away from package section 22, to expose valve 12.

Referring to FIG. 4, a mitral valve 52 for implantation in an excised mitral orifice of a human heart is shown in a valve package 10a. The valve package is largely identical with the valve package of FIGS. 1 through 3, but with the following modifications.

It will be noted that mitral valve 52 carries a pair of parallel, U-shaped struts 54, which are mounted in spaced relation to each other, and which retain a disc-shaped closure member 56, which reciprocates upward and downward to open and close an orifice in valve ring 58.

Package sections 20a and 22a are essentially similar in construction to the previously disclosed package sections 20 and 22. Section 22a contains a resilient pad 24a, which is also essentially similar in construction to its corresponding member in FIGS. 1 through 3, pad 24. Retainer member 60, however, is of different construction, being a strip of rigid plastic, narrow enough to lie between spaced struts 54. Retainer member 60 presses against the top of closure member 56, to bias valve 52 into the resilient pad 24a in a manner similar to that previously disclosed. The ends of strip 60 rest against shoulders 44a, to permit retainer member 60 to be biased against valve 52, while at the same time permitting relative axial motion between retainer member 60 and the package sections 20a and 22a as the package is being opened, to avoid placing substantial torque on the struts 54.

Referring to FIGS. 5 through 7, the package sections 20b and 22b remain essentially identical to sections 20 and 22 previously described. O-ring 34b is also used in a manner similar to O-ring 34.

Resilient pad 62, however, defines cut-out portions 64, 66 (FIG. 6) which are proportioned in size and shape to receive struts 54 of a heart valve (for example the mitral valve 52 previously shown in FIG. 4). In this embodiment, mitral valve 52 is stored in inverted position, with struts 54 inserted within cut-out portions 64, 66.

Retainer member 68 which is shown separately in FIG. 7, bears against the upper surface of inverted valve 52 to bias the valve, in a manner similar to that previously described, against resilient pad 62. Hence, struts 54 are inserted in cut-out portion 64, 66 and a central portion 70 of the upper surface of resilient pad 62 bears against closure member 56, holding it firmly in closed position against the valve ring 58.

End portions 72 of retainer 68 are proportioned so that annular shoulder 44b of package section 20b bears against it to provide biasing pressure to valve 52, urging it into the resilient pad for maximum protection against dropping and other shocks during transit.

In both embodiments of FIGS. 4 and 5, the other package section 22a, 22b is spaced from retainer 60, 68 in a manner similar to the embodiment of FIG. 1.

If desired, an aperture 74 can be placed in retainer member 68 or 60 for visual observation of the valve, and to facilitate sterilization of the side of the valve in contact with the retainer member.

Both packages 22a to 22b define apertures 38a and 38b, corresponding to aperture 38 of FIG. 1, as well as filter members corresponding to filter member 40, and having similar function.

The above has been offered for illustrative purposes only, and is not to be interpreted as restricting the invention of this application, which is as described in the claims below.

That which is claimed is:

1. In a package for prosthetic heart valve and the like comprising a pair of separable, mating package sections for receiving said heart valve, and retaining said valve in sterile manner in biased position against a resilient pad carried by one of said package sections, the improvement comprising:
    (a) a separate retainer member positioned within said package for biasing said heart valve against the resilient pad, said retainer being a rigid sheet having an aperture shaped to receive a portion of said valve, and
    (b) a shoulder defined in one of said mating package sections, said shoulder being adapted to urge the retainer member into a biased position against the heart valve so that the heart valve is in turn biased against the resilient pad, said shoulder being further adapted to slide easily along the surface of the retainer member so that torque is not transmitted to the heart valve when the mating package sections are rotated to open or close the package.

2. The package of claim 1 in which said package sections each define a cylindrical mating portion adapted for telescoping, mating relation with the mating portion of the other package section, said mating portions each defining helically mating thread and groove closure means, for closing said package sections together into a sealed package by relative movement.

3. The package of claim 2 in which an annular sealing means is positioned between the cylindrical mating portions in a position to seal said helical thread and groove means from the exterior.

4. The package of claim 1 in which an aperture is defined in the package section which carries the resilient pad, said aperture being covered by said resilient pad, and a porous filter member which is positioned on the inner wall of said package section across said aperture.

5. The package of claim 1 in which said aperture is proportioned for receiving a ball-type closure member and a retention cage of a ball-type heart valve, said aperture comprising a round, closure member-receiving central portion, and a plurality of elongated, radial, retention cage-receiving portions.

6. In a package containing a prosthetic heart valve which includes a pair of separable, mating package sections for receiving such heart valve, and a resilient pad positioned in one of said package sections, the improvement which is a separate retainer member adapted to urge said heart valve against said resilient pad, said retainer member being positioned within the package when the two package sections are mated so that it is spaced from the package section containing the pad and in contact with although not connected to the other package section, said retainer member being adapted not to rotate with either of the package sections so that torque is not transmitted to the heart valve when the mating package sections are rotated relative to each other for opening and closing the package.

* * * * *